US009700447B2

(12) United States Patent
Von Oepen et al.

(10) Patent No.: US 9,700,447 B2
(45) Date of Patent: Jul. 11, 2017

(54) SURFACE INTERACTIONS TO IMPROVE RETENTION OF MEDICAL DEVICES

(71) Applicant: Abbott Laboratories, Abbott Park, IL (US)

(72) Inventors: Randolf Von Oepen, Los Altos Hills, CA (US); John L. Toner, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 14/968,707

(22) Filed: Dec. 14, 2015

(65) Prior Publication Data
US 2016/0100967 A1 Apr. 14, 2016

Related U.S. Application Data

(62) Division of application No. 11/742,441, filed on Apr. 30, 2007, now Pat. No. 9,220,812.

(60) Provisional application No. 60/796,569, filed on May 1, 2006.

(51) Int. Cl.
| *A61F 2/958* | (2013.01) |
| *A61L 29/08* | (2006.01) |
| *A61L 29/14* | (2006.01) |
| *A61L 31/10* | (2006.01) |
| *A61L 31/14* | (2006.01) |
| *A61L 31/08* | (2006.01) |

(52) U.S. Cl.
CPC ............ *A61F 2/958* (2013.01); *A61L 29/085* (2013.01); *A61L 29/14* (2013.01); *A61L 31/08* (2013.01); *A61L 31/10* (2013.01); *A61L 31/14* (2013.01); *A61F 2002/9583* (2013.01)

(58) Field of Classification Search
CPC ............ A61F 2/958; A61F 2002/9583; A61L 29/085; A61L 31/08; A61L 31/10; A61L 31/14; A61L 29/14
See application file for complete search history.

(56) References Cited

U.S. PATENT DOCUMENTS

| 5,498,659 | A | * | 3/1996 | Esser | ..................... C08F 8/32 524/522 |
| 6,245,076 | B1 | * | 6/2001 | Yan | ........................... A61F 2/95 604/96.01 |
| 6,884,842 | B2 | * | 4/2005 | Soane | ................. C08B 37/0021 424/450 |
| 9,220,812 | B2 | | 12/2015 | Von Oepen et al. | |
| 9,283,099 | B2 | * | 3/2016 | Gale | ........................ A61F 2/958 |
| 2003/0083433 | A1 | | 5/2003 | James et al. | |

FOREIGN PATENT DOCUMENTS

| WO | WO 02/24115 | 3/2002 |
| WO | WO 2007/130366 A3 | 11/2007 |

OTHER PUBLICATIONS

Cram et al, 1987, The design of molecular hosts, guests, and their complexes. Nobel Lectures, Chemistry, 1981-1990: 419-437.
Invitation to Pay Additional Fees for PCT/US2007/010481, mailed Jul. 9, 2008, 10 pgs, and the International Search Report mailed Oct. 22, 2008, 17 pgs.
"Adhesion and Cohesion," Copyright 2010, Printed Apr. 13, 2011, www.adhesives.org/TrainingEducation/StudentResources/Adhesionandcohesion.aspx, 2 pages.
Written Opinion of the International Searching Authority for International Application No. PCT/US2007/010481 filed Apr. 30, 2007, 7 pages.
Stone et al, Characterization of a Transient Covalent Adduct Formed during Dimethylarginine Dimethylaminohydrolase Catalysist (2005) *Biochemistry*, http://pubs.acs.org/doi/abs/10.1021/bi047407r, Abstract only, 1 page.
Di Jeso, et al., Transient Covalent Interactions of Newly Synthesized Thyroglobulin with Oxidoreductases of the Endoplasmic Reticulum (2014) *The Journal of Biological Chemistry* 289(16):11488-11496.
Nelson et al., Lehninger *Principles of Biochemistry* $4^{th}$ Edition, W.H. Freeman and Associates, 2004; Chapter 6: Enzymes pp. 190-237.

* cited by examiner

*Primary Examiner* — Suzanne Ziska
(74) *Attorney, Agent, or Firm* — Squire Patton Boggs (US) LLP

(57) ABSTRACT

A method for improving the retention between the surfaces of medical devices. The method includes coating a surface of one medical device such as a stent with a coating that includes a functional group and coating a surface of another medical device such as a balloon with a coating that includes an identical or different functional group. The method further includes interacting the coated surfaces to produce a plurality of bonds between the surfaces, thereby improving retention.

6 Claims, 3 Drawing Sheets

SURFACE INTERACTIONS TO IMPROVE RETENTION OF MEDICAL DEVICES

CROSS-REFERENCE TO RELATED APPLICATIONS

This application is a division of U.S. patent application Ser. No. 11/742,441, filed on Apr. 30, 2007, published as US 2007/0264305 A1 on Nov. 15, 2007, and issued as U.S. Pat. No. 9,220,812, on Dec. 29, 2015, which claims the benefit of U.S. Provisional Application No. 60/796,569, filed on May 1, 2006, the entire disclosure of both of which are incorporated herein by reference, and the incorporation by reference herein of U.S. patent application Ser. No. 11/742,441 expressly includes any drawings.

BACKGROUND OF THE INVENTION

Field of the Invention

This invention relates to medical devices. Particularly, it relates to stent devices and balloon catheter devices. More particularly, it relates to the retentive interactions between these medical devices when they are assembled as stent delivery systems and used in a variety of medical procedures to treat medical conditions in animal and human patients.

Description of Related Art

The use of medical devices for treating medical conditions in patients is well known. In particular, medical devices are commonly used during the treatment of vascular conditions involving lesions that block blood flow within body vessels. These procedures usually require that the medical devices be delivered to the treatment site by accessing and tracking through the vessel system.

The medical devices used in these types of procedures include stent delivery systems. Stent delivery systems generally have a stent component (bare metal or drug coated) disposed on the balloon of a balloon catheter component. The stent component must be retained on the balloon during storage and delivery to the treatment site, prior to deployment.

Various methods exist for retaining the stent on the balloon. The most commonly used method is crimping the stent onto the balloon. This is done during a process that is either part of the device manufacture, or it is performed by the physician prior to inserting the stent delivery system within the patient. In general, the stent crimping process involves an inward radial load applied to the stent while it circumferentially encompasses the balloon. The radial load brings the surfaces of the stent and balloon in contact, and the resulting surface friction produces a retaining force. The crimping process usually includes temperature and pressure applied to the stent and balloon surfaces over a period of time. The efficacy of this method is limited by the frictional characteristics of the stent and balloon, as well as by the limits of the pressure and temperature that can be applied without damaging the surface or surface coatings of the stent and balloon. Especially in drug-eluting stents, the polymer drug-containing coatings limit the temperatures and pressures that can be used in the crimping process without significantly damaging coating integrity, coating elution kinetics, and drug potency.

In addition to crimping, means have been developed to improve stent retention during storage and delivery. For instance, features have been provided on the balloon that resists axial movement of the stent. For example, the ends of the balloon have been modified to create pillowed sections with outer diameters approximately the same as the crimped stent diameter. The pillowed balloon section is meant to resist axial movement of the stent by creating an obstruction and reactive load if the stent slides axially during delivery. Similarly, features such as bumps, ridges, and the like have been formed on the balloon to obstruct and resist stent movement. The drawbacks of this method include complicated balloon manufacturing processes, potential weakening of the balloon material, and increased system profile resulting in less deliverability.

An alternative method for improving stent retention involves the use of adhesives to bond the stent to the balloon. This method includes the steps of applying an adhesive to the stent, balloon, or both, and then bringing the component surfaces into contact. The resulting adhesion is intended to resist the dislodgement forces applied during storage and delivery of the stent. The drawbacks of this method include potential weakening of the balloon material, excessive deformation of the stent pattern during deployment, and additional steps during stent delivery and deployment.

Another solution for improving stent retention is to provide a sheath that surrounds the stent. The sheath is removed from the stent prior after delivery to the treatment site and prior to stent deployment. This solution is intended to reduce the dislodgement loads applied to the stent during storage and delivery. The drawbacks of this solution include the requirement for additional delivery steps and the increase in system profile.

The present invention is aimed at improving stent retention while avoiding the shortcomings associated with prior solutions. The object of the present invention is to improve the retention between medical devices by providing a coating on the surface of one medical device that interacts with a coating provided on the surface of another medical device. This invention avoids potential tradeoffs between increased stent retention and issues such as coating integrity, coating elution kinetics, drug potency, weakened balloon material, additional deployment steps, excessive profile, etc., associated with prior solutions.

SUMMARY OF THE INVENTION

The purpose and advantages of the present invention will be described and apparent from the description that follows, and through practice of the invention.

To achieve these purposes and advantages, and in accordance with the present invention, a method is provided for improving the retention between surfaces of coatings of medical devices. The method includes coating a surface of one medical device such as a stent with a coating that includes a hydrogen bond donor and coating a surface of another medical device such as a balloon with a coating that includes a suitable acceptor atom or molecule. The method further includes interacting the coated surfaces to produce a plurality of hydrogen bonds between the surfaces, thereby improving retention.

In an alternative embodiment of the present invention, a method is provided for improving the retention between surfaces of coatings of medical devices. The method includes coating a surface of one medical device such as a stent with a coating that includes a host molecule and coating a surface of another medical device such as a balloon with a coating that includes a guest atom or molecule. The method further includes interacting the coated surfaces to produce a plurality of covalent bonds between the surfaces, thereby improving retention.

In an alternative embodiment of the present invention, a method is provided for improving the retention between surfaces of coatings of medical devices. The method includes coating a surface of one medical device such as a stent with a coating that includes a donor molecule and coating a surface of another medical device such as a balloon with a coating that includes an acceptor. The method further includes interacting the coated surfaces to produce a plurality of electron donor-acceptor complexes between the surfaces, thereby improving retention.

In an alternative embodiment of the present invention, a method is provided for improving the retention between surfaces of coatings of medical devices. The method includes coating a surface of one medical device such as a stent with a coating that includes a dipolar functional group and coating a surface of another medical device such as a balloon with a coating that includes a charged functional unit. The method further includes interacting the coated surfaces to produce a plurality of charge-dipole interactions between the surfaces, thereby improving retention.

In an alternative embodiment of the present invention, a method is provided for improving the retention between surfaces of coatings of medical devices. The method includes coating a surface of one medical device such as a stent with a coating that includes a dipolar functional group and coating a surface of another medical device such as a balloon with a coating that includes a dipole functional unit. The method further includes interacting the coated surfaces to produce a plurality of dipole-dipole interactions between the surfaces, thereby improving retention.

In an alternative embodiment of the present invention, a method is provided for improving the retention between surfaces of coatings of medical devices. The method includes coating a surface of one medical device such as a stent with a coating that includes a charged functional group and coating a surface of another medical device such as a balloon with a coating that includes a charged functional unit. The method further includes interacting the coated surfaces to produce a plurality of charge-charge interactions between the surfaces, thereby improving retention.

In an alternative embodiment of the present invention, a method is provided for improving the retention between surfaces of coatings of medical devices. The method includes coating a surface of one medical device such as a stent with a coating that includes a hydrophobic group and coating a surface of another medical device such as a balloon with a coating that includes a hydrophobic group. The method further includes interacting the coated surfaces to produce a plurality of hydrophobic interactions between the surfaces, thereby improving retention.

In an alternative embodiment of the present invention, a method is provided for improving the retention between surfaces of coatings of medical devices. The method includes coating a surface of one medical device such as a stent with a coating that includes a pendant activated carboxylate group and coating a surface of another medical device such as a balloon with a coating that includes a pendant amine group. The method further includes interacting the coated surfaces to produce a plurality of transient covalent linkages between the surfaces, thereby improving retention.

In an alternative embodiment of the present invention, a method is provided for improving the retention between surfaces of coatings of medical devices. The method includes coating a surface of one medical device such as a stent with a coating that includes any of the previously mentioned donors, acceptors, atoms, molecules, and groups and coating a surface of another medical device such as a balloon with a coating that includes any of the previously mentioned donors, acceptors, atoms, molecules, and groups. The method further includes interacting the coated surfaces to produce a plurality of bonds, interactions, or linkages between the surfaces, thereby improving retention.

In further accordance with the present invention, there is a combination of medical devices comprising one medical device having a surface treated with any of the methods heretofore recited and another medical device having a surface treated with any of the methods heretofore recited, wherein the surface coatings of the medical devices interact to form a plurality of bonds, interactions, or linkages that improve retention between the medical devices.

In further accordance with the present invention, the medical devices heretofore recited include the stent and balloon components of a stent delivery system.

BRIEF DESCRIPTION OF THE DRAWINGS

For a further appreciation of the above and other advantages, reference is made to the detailed description and to the drawings, in which.

DETAILED DESCRIPTION OF THE PREFERRED EMBODIMENTS

Figure 1:
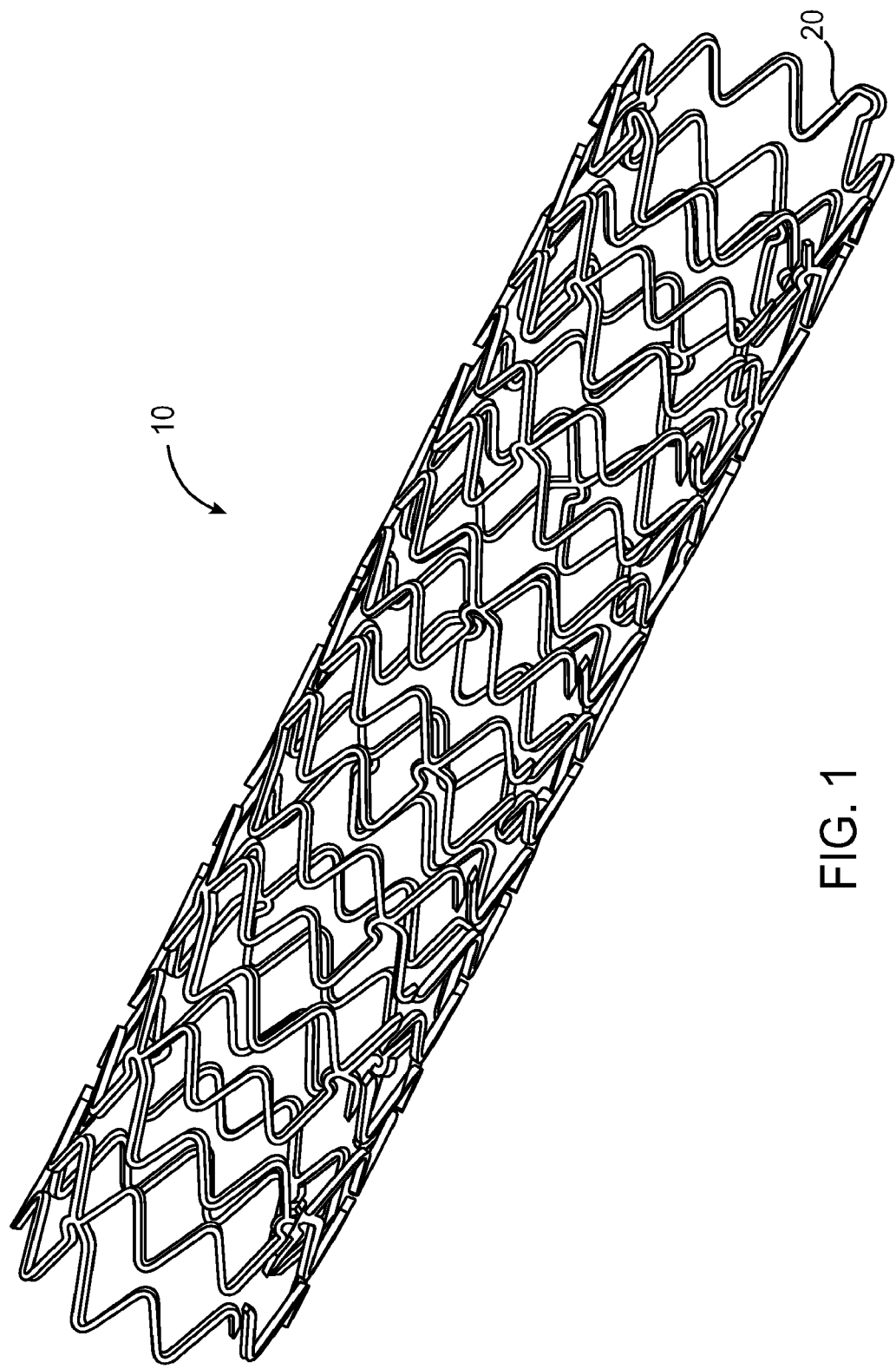
FIG. 1 is a perspective view of a stent medical device in accordance with the present invention illustrating the stent in an undeployed configuration.

While the present invention will be described in detail with reference to a few specific embodiments, the description is illustrative and is not to be construed as limiting the invention. Various modifications can be made to the preferred embodiments by those skilled in the art without departing from the spirit and scope of the invention as defined by the appended claims. It will be noted here that for a better understanding, like components have been designated by like reference numerals through the various accompanying figures.

In accordance with the present invention there is provided a method for improving the retention between surfaces of medical devices, having the steps of coating the surfaces of both medical devices, and then interacting the surfaces to create bonds, interactions, or linkages between the coated surfaces. The invention is particularly useful for increasing the retention force between a stent 10 and balloon 60 of a stent delivery system 70, thereby improving the deliverability of the system through vessels. The invention has additional advantages that will be apparent from the forthcoming detailed description.

Figure 2:
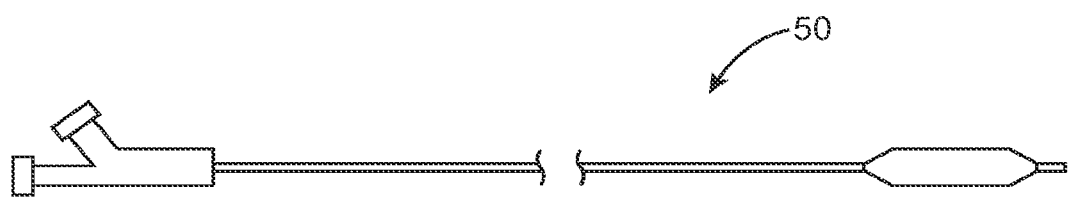
FIG. 2 is a plan view of a balloon catheter medical device in accordance with the present invention.
Figure 3:
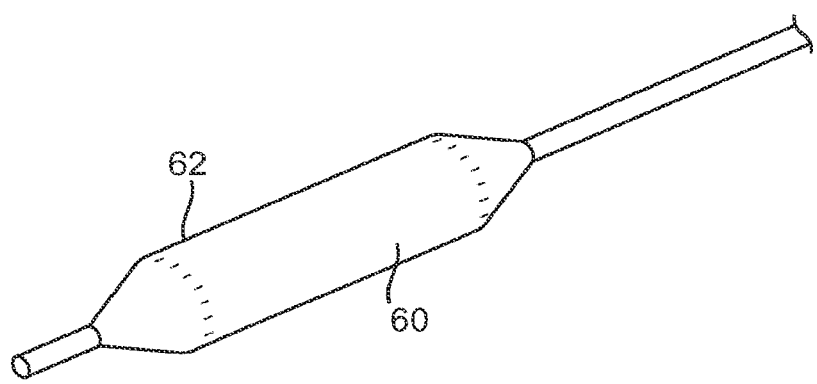
FIG. 3 is a partial perspective view of a distal end portion of a balloon catheter medical device in accordance with the present invention illustrating a balloon component disposed thereon.
Figure 4:
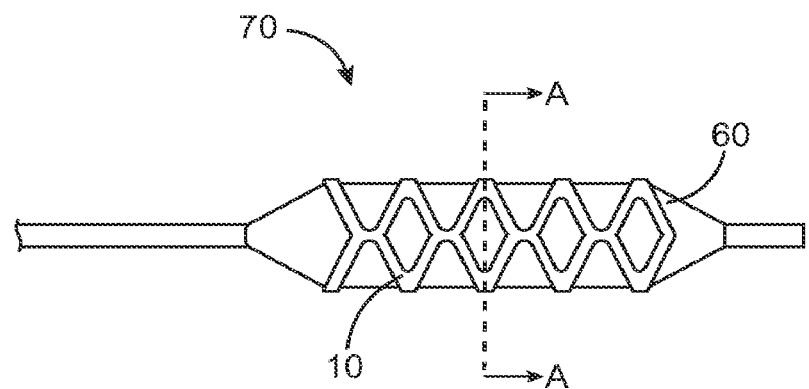
FIG. 4 is a partial plan view of the distal end portion of a stent delivery system in accordance with the present invention illustrating a balloon component with a stent disposed thereon.
Figure 5:
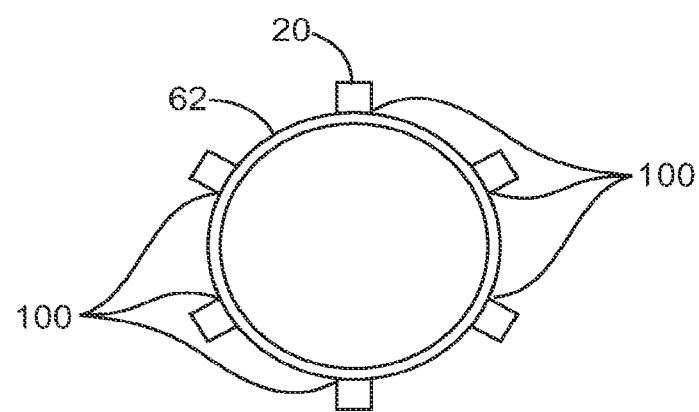
FIG. 5 is a cross-sectional view of a stent delivery system in accordance with the present invention taken about line A-A of FIG. 4, illustrating the interaction of the stent and balloon surfaces.

Referring now to FIG. 1, there is shown a stent 10 having a stent surface 20. The stent 10 is shown in an unexpanded configuration, which is representative of the as-cut configuration. Referring now to FIG. 2, there is shown a balloon catheter device 50. In this drawings, the balloon catheter device 50 is an over-the-wire type catheter, however it can also be a rapid exchange type catheter to fulfill the purposes of this invention. Referring now to FIG. 3, there is shown a balloon 60 disposed on a distal end portion of the balloon catheter device 50. The balloon 60 has a balloon surface 62. Referring now to FIG. 4, there is shown a distal end portion of a stent delivery system 70. The stent delivery system 70 includes a stent 10 and balloon 60 in proximity with each other after undergoing a crimping and heat setting process. Referring now to FIG. 5, there is shown a cross-sectional view of the stent delivery system 70 in accordance with the present invention taken about line A-A of FIG. 4. The stent surface 20 and balloon surface 62 are shown to be in contact at various surface interaction points 100.

In an exemplary embodiment of the present invention, a method is provided for improving the retention between a stent surface 20 and a balloon surface 62 of a stent delivery system 70. The method includes spray coating the balloon surface 62 with a polymer having an appropriate hydrogen bond donor (A). Preferably the hydrogen bond donor (A) is an alkyl alcohol or amide N—H group that is linked to the polymer.

In further accordance with the present invention, the method further includes spray coating the stent surface 20 with a polymer having suitable acceptor molecules (B). Preferably the acceptor molecules (B) are corbonyls of esters, amides, hydroxamides, ketones, or aldehydes.

The method further includes using crimping and heat setting steps to place the stent surface 20 and balloon surface 62 in proximity. The hydrogen bond donor (A) and acceptor molecules (B) interact to produce numerous hydrogen bonds between the stent surface 20 and the balloon surface 62. In hydrogen bonding, a weak bond forms between a functional group A-H and an atom or group of atoms B in the same or different molecules. The aggregate strength of these numerous bonds results in an increase in retention between the two medical device surfaces.

In an alternative embodiment of the present invention, the total retention force between the medical device surfaces may be adjusted. This can be achieved by modifying the density of the functional groups on the medical device surfaces. Alternatively, the projected distance of the functional groups from the polymer surface (by utilizing pendant groups) may be modified.

In accordance with the present invention, there is a combination of the stent 10 and balloon catheter device 50 produced according to the aforementioned method. The combination of medical device from a stent delivery system 70. The stent delivery system 70 is useful for the treatment of medical conditions such as diseased coronary vessels. The stent delivery system 70 can be inserted within and delivered through the vascular system to the treatment site, which may be a lesion, for example. During storage and delivery, there are dislodgement forces applied to the stent 10. The improved retention between the stent 10 and balloon 60 resist these forces, and help ensure effective delivery of the stent 10 to the treatment site.

In particular, the improved retention and resistance of the stent delivery system 70 to stent dislodgement is useful during the treatment of bifurcated vessels with bifurcation stent delivery systems. In the case of a bifurcation stent delivery system, the stent 10 may be only partially crimped onto the balloon 60. Also, a guidewire may be placed through the stent strut, providing an additional dislodgement force to the stent 10 as the stent 10 is delivered to the target site. Therefore, the improved stent retention plays a vital role in facilitating effective stent delivery and deployment.

Once in place, the stent 10 is deployed by inflating the balloon 60. The bonds formed between the stent 10 and balloon 60 are broken by this deployment, permitting the stent 10 to expand and appose the vessel within the treatment site.

Alternative Embodiment

In an alternative embodiment of the present invention, a method is provided for improving the retention between a stent surface 20 and a balloon surface 62 of a stent delivery system 70. The method includes spray coating the balloon surface 62 with a solution or suspension of a polymer having an appropriate host molecule (A). Preferably the host molecule (A) is a pendant crown ether, podand, polyether, substituted polyether, cryptand, hemispherand, or spherand unit that is linked to the polymer.

In further accordance with the present embodiment, the method further includes spray coating the stent surface 20 with a polymer having suitable guest atoms or molecules (B). Preferably the guest atoms or molecules (B) are from the pendant alkyl ammonium, substituted alkyl ammonium, aryl, substituted aryl ammonium, positively charged heterocyles, metal carboxylates, metal phenolates, metal hydroxamates, or other metal organic salt groups.

The method further includes using crimping and heat setting steps to place the stent surface 20 and balloon surface 62 in proximity. The host molecules (A) and guest atoms or molecules (B) interact to produce numerous host-guest interactions between the stent surface 20 and the balloon surface 62. A host-guest interaction (complex) occurs when a host molecule forms a non-covalent interaction with a guest atom or molecule and organizes structurally to partially or completely surround or enclose the guest. The process is often referred to as complexation. The aggregate strength of these numerous interactions results in an increase in retention between the two medical device surfaces.

In an alternative embodiment of the present invention, the total retention force between the medical device surfaces may be adjusted. This can be achieved by modifying the density of the functional groups on the medical device surfaces. Alternatively, the projected distance of the functional groups from the polymer surface (by utilizing pendant groups) may be modified.

Alternative Embodiment

In an alternative embodiment of the present invention, a method is provided for improving the retention between a stent surface 20 and a balloon surface 62 of a stent delivery system 70. The method includes spray coating the balloon surface 62 with a solution or suspension of a polymer having an appropriate acceptor molecule (A). Preferably the acceptor molecule (A) is a covalently linked picric acid that is linked to the polymer. Alternatively, the acceptor molecule may be a nitroaromatic, anhydride or tetracyanoethylene.

In further accordance with the present embodiment, the method further includes spray coating the stent surface 20 with a polymer having suitable donor molecules (B). Preferably the donor molecules (B) are from the aromatic hydrocarbon, aromatic amine, aliphatic amine, and olefin groups.

The method further includes using crimping and heat setting steps to place the stent surface 20 and balloon surface 62 in proximity. The acceptor molecules (A) and donor molecules (B) interact to produce numerous electron donor-acceptor (EDA) complexes between the stent surface 20 and the balloon surface 62. An EDA complex forms when a donor molecule donates an unshared pair of electrons (a n donor) or a pair of electrons in a π orbital of a double bond or aromatic system (a π donor). The aggregate strength of these numerous complexes results in an increase in retention between the two medical device surfaces.

In an alternative embodiment of the present invention, the total retention force between the medical device surfaces may be adjusted. This can be achieved by modifying the density of the functional groups on the medical device surfaces. Alternatively, the projected distance of the functional groups from the polymer surface (by utilizing pendant groups) may be modified.

Alternative Embodiment

In an alternative embodiment of the present invention, a method is provided for improving the retention between a stent surface 20 and a balloon surface 62 of a stent delivery system 70. The method includes spray coating the balloon surface 62 with a solution or suspension of a polymer having dipolar group (A). Preferably the dipolar group (A) is a phosphonate. Alternatively, the dipolar group may be from the carbonyl group such as ketones, aldehydes, esters, amides, carbonates, and carbamates. Further still, the dipolar group may be a phosphine oxide, sulfoxide, sulfonamide, sulfone, pyridine N-oxide, alkyl or aryl ether.

In further accordance with the present embodiment, the method further includes spray coating the stent surface 20 with a polymer having charged group (B). Preferably the charged group (B) is phosphoryl choline such as found in PC1036. Alternatively, the charged group may be from the phosphoryl ethanolamine, carboxylate, quaternary amine, protonated amine, pyridinium compound, other positively charged heterocyclic compound, phenolates, hydroxamates, thiocarboxylates, sulfates, sulfonates, phosphates, phosphonates, sulfides, or stabilized carbanions groups.

The method further includes using crimping and heat setting steps to place the stent surface 20 and balloon surface 62 in proximity. The dipolar group (A) and charged group (B) interact to produce numerous charge-dipole interactions between the stent surface 20 and the balloon surface 62. A dipole exists in organic functional groups that intrinsically have partial internal charge separation, such as the partial positive charge on a carbonyl carbon atom and the partial negative charge on the carbonyl oxygen atom. The aggregate strength of these numerous charge-dipole interactions results in an increase in retention between the two medical device surfaces.

In an alternative embodiment of the present invention, the total retention force between the medical device surfaces may be adjusted. This can be achieved by modifying the density of the functional groups on the medical device surfaces. Alternatively, the projected distance of the functional groups from the polymer surface (by utilizing pendant groups) may be modified.

Alternative Embodiment

In an alternative embodiment of the present invention, a method is provided for improving the retention between a stent surface 20 and a balloon surface 62 of a stent delivery system 70. The method includes spray coating the balloon surface 62 with a solution or suspension of a polymer having dipolar functional group (A). Preferably the dipolar functional group (A) is a phosphonate. Alternatively, the dipolar functional group may be from the carbonyl group such as ketones, aldehydes, esters, amides, carbonates, and carbamates. Further still, the dipolar functional group may be a phosphine oxide, sulfoxide, sulfonamide, sulfone, pyridine N-oxide, alkyl or aryl ether.

In further accordance with the present embodiment, the method further includes spray coating the stent surface 20 with a polymer having dipolar functional unit (B). Preferably the dipolar functional unit (B) is an amide. Alternatively, the dipolar functional unit may be from the carbonyl group such as ketones, aldehydes, esters, carbonates, and carbamates. Further still, the dipolar functional unit may be a phosphonate, phosphine oxide, sulfoxide, sulfonamide, sulfone, pyridine N-oxide, alkyl or aryl ether.

The method further includes using crimping and heat setting steps to place the stent surface 20 and balloon surface 62 in proximity. The dipolar function group (A) and dipolar functional unit (B) interact to produce numerous dipole-dipole interactions between the stent surface 20 and the balloon surface 62. A dipole exists in organic functional groups that intrinsically have partial internal charge separation, such as the partial positive charge on a carbonyl carbon atom and the partial negative charge on the carbonyl oxygen atom. The aggregate strength of these numerous dipole-dipole interactions results in an increase in retention between the two medical device surfaces.

In an alternative embodiment of the present invention, the total retention force between the medical device surfaces may be adjusted. This can be achieved by modifying the density of the dipolar groups on the medical device surfaces. Alternatively, the projected distance of the dipolar groups from the polymer surface (by utilizing pendant groups) may be modified.

Alternative Embodiment

In an alternative embodiment of the present invention, a method is provided for improving the retention between a stent surface 20 and a balloon surface 62 of a stent delivery system 70. The method includes spray coating the balloon surface 62 with a solution or suspension of a polymer having charged functional group (A). Preferably the charged functional group (A) is a carboxylate group. Alternatively, the charged functional group may be another negatively charged group such as ethanolamine, phenolates, hydroxamates, thiocarboxylates, sulfates, sulfonates, phosphates, phosphonates, sulfides, or stabilized carbanions. Further still, the charged functional group may be a positively charged group such as quaternary amines, protonated amines, pyridinium compounds, and phosphoryl choline.

In further accordance with the present embodiment, the method further includes spray coating the stent surface 20 with a polymer having charged functional unit (B), either the same as the charged functional group (A), or others. Preferably the charged functional unit (B) is a zwitterionic phosphoryl choline unit. Alternatively, the charged functional group may be another positively charged group such as quaternary amines, protonated amines, pyridinium compounds, and phosphoryl choline. Further still, the charged functional group may be a negatively charged group such as ethanolamine, carboxylate, phenolates, hydroxamates, thiocarboxylates, sulfates, sulfonates, phosphates, phosphonates, sulfides, or stabilized carbanions.

The method further includes using crimping and heat setting steps to place the stent surface 20 and balloon surface 62 in proximity. The charged functional group (A) and charged functional unit (B) interact to produce numerous charge-charge interactions between the stent surface 20 and the balloon surface 62. The aggregate strength of these numerous charge-charge interactions results in an increase in retention between the two medical device surfaces.

In an alternative embodiment of the present invention, the total retention force between the medical device surfaces may be adjusted. This can be achieved by modifying the density of the charge groups on the medical device surfaces.

Alternatively, the projected distance of the charge groups from the polymer surface (by utilizing pendant groups) may be modified.

Alternative Embodiment

In an alternative embodiment of the present invention, a method is provided for improving the retention between a stent surface 20 and a balloon surface 62 of a stent delivery system 70. The method includes spray coating the balloon surface 62 with a solution or suspension of a polymer having hydrophobic group (A). Preferably the hydrophobic group (A) is a stearoyl group. Alternatively, the hydrophobic group may be a long-chain alkyl, substituted alkyl, fatty acid, fatty ester, aryl, or polyaryl units.

In further accordance with the present embodiment, the method further includes spray coating the stent surface 20 with a polymer having another hydrophobic group (B), either the same as the hydrophobic group (A). Preferably the hydrophobic group (B) is a stearoyl group. Alternatively, the hydrophobic group may be a long-chain alkyl, substituted alkyl, fatty acid, fatty ester, aryl, or polyaryl units.

The method further includes using crimping and heat setting steps to place the stent surface 20 and balloon surface 62 in proximity. The hydrophobic group (A) and hydrophobic group (B) interact to produce numerous hydrophobic interactions between the stent surface 20 and the balloon surface 62. The aggregate strength of these numerous hydrophobic interactions results in an increase in retention between the two medical device surfaces.

In an alternative embodiment of the present invention, the total retention force between the medical device surfaces may be adjusted. This can be achieved by modifying the density of the hydrophobic groups on the medical device surfaces. Alternatively, the projected distance of the hydrophobic groups from the polymer surface (by utilizing pendant groups) may be modified.

Alternative Embodiment

In an alternative embodiment of the present invention, a method is provided for improving the retention between a stent surface 20 and a balloon surface 62 of a stent delivery system 70. The method includes spray coating the balloon surface 62 with a solution or suspension of a polymer having a functional group (A) in an activated state. Preferably the functional group (A) is a pendant carboxylate group.

In further accordance with the present embodiment, the method further includes spray coating the stent surface 20 with a polymer having another functional group (B) in an activated state that is capable of reacting with functional group (A). Preferably the functional group (B) is a pendant amine group.

The method further includes using crimping and heat setting steps to place the stent surface 20 and balloon surface 62 in proximity. The functional group (A) and functional group (B) react with each other to produce numerous transient covalent linkages between the stent surface 20 and the balloon surface 62. The aggregate strength of these numerous covalent linkages results in an increase in retention between the two medical device surfaces.

Alternatively, the functional groups may be applied and activated afterward. Further still, an additional reagent may be used to improve the reaction between the functional groups. For example, the use of pyridine in the reaction of acyl halides with alcohols.

Further still, a large number of reactions are useful for improving stent retention, including those that form esters, amides, carbon-carbon bonds, thioesters, thioamides, hydroxamic acid, hydrazones, semicarbazones, imines, ethers, thioethers, and disulphides.

In an alternative embodiment of the present invention, the total retention force between the medical device surfaces may be adjusted. This can be achieved by modifying the number and type of covalent linkages.

Alternative Embodiment

In an alternative embodiment of the present invention, the heretofore-recited methods may be combined to improve retention between a stent surface 20 and a balloon surface 62 of a stent delivery system 70.

In accordance with the present embodiment, the combined method further includes spray coating the balloon surface 62 with a polymer having a hydrogen bond donor such as amide N—H group. Alternatively, the balloon surface 62 may be modified using any of the aforementioned coating methods.

The method further provides applying a solution of an appropriate pharmaceutically acceptable agent such as zotarolimus to the balloon surface 62. Alternatively, dexamethasone may be applied to the balloon surface 62.

In accordance with the present embodiment, the method further includes spray coating the stent surface 20 with a polymer having hydrogen bond acceptor groups such as amide carbonyls. Alternatively, the stent surface 20 may be modified using any of the aforementioned coating methods.

The method further includes using crimping and heat setting steps to place the stent surface 20 and balloon surface 62 in proximity, thereby forming hydrogen bonds. Additionally, the presence of zotarolimus improves stent retention between the stent surface 20 and balloon surface 62 through adhesion.

In an alternative embodiment of the present invention, the total retention force between the medical device surfaces may be adjusted. This can be achieved by modifying the density of the functional groups on the medical device surfaces. Alternatively, the projected distance of the functional groups from the polymer surface (by utilizing pendant groups) may be modified. Further still, varying the concentration of zotarolimus will adjust retention.

The invention claimed is:

1. A method for improving the retention between surfaces of coatings of medical devices, comprising:
   providing a plurality of coated medical devices each having a surface, wherein one said medical device having a coating surface comprising a first functional group and another said medical device having a coating surface comprising a second functional group;
   wherein the first functional group is a pendant carboxylate group; and
   wherein the second functional group is a pendant amine group; and
   interacting said surface including the first functional group with said surface comprising the second functional group to produce a plurality of transient covalent linkages between said surfaces for improving retention between said medical devices.

2. The method of claim 1, further comprising:
   providing a reagent to improve the reaction between the first functional group and the second functional group.

3. The method of claim 1, further comprising:
   reacting the first functional group with the second functional group to form a product.

4. The method of claim 1, wherein the medical devices are selected from the group consisting of stents and balloons.

5. A combination of medical devices, comprising:
   a plurality of coated medical devices each having a surface, wherein one said medical device having a coating surface including comprising pendant activated carboxlate groups and another said medical device having a coating surface comprising pendant amine groups, wherein said surface comprising pendant activated carboxlate groups bonds with said surface comprising pendant amine groups to produce a plurality of transient covalent linkages between said surfaces for improving retention between said medical devices.

6. The combination of medical devices of claim 5, wherein the medical devices are selected from the group consisting of stents and balloons.

* * * * *